United States Patent
Gajewski et al.

Patent Number: 5,447,343
Date of Patent: Sep. 5, 1995

[54] RIGID ENDOSCOPE CONNECTOR

[75] Inventors: Mark T. Gajewski, Chapel Hill; Stephen B. Leonard, Fuquay Varina; David E. Shoff, Raleigh, all of N.C.

[73] Assignee: American Sterilizer Company, Erie, Pa.

[21] Appl. No.: 128,799

[22] Filed: Sep. 28, 1993

[51] Int. Cl.⁶ .................. A61M 39/12; A61M 39/16; F16L 37/12
[52] U.S. Cl. .................................. 285/317; 285/308; 403/325; 600/133
[58] Field of Search .............. 403/322, 325; 285/305, 285/308, 317; 128/4, 6

[56] References Cited

U.S. PATENT DOCUMENTS

| | | | |
|---|---|---|---|
| 4,311,328 | 1/1982 | Truchet | 285/308 |
| 4,436,125 | 3/1984 | Blenkush | 285/308 |
| 4,863,201 | 9/1989 | Carstens | 285/308 |

Primary Examiner—Richard A. Berisch
Assistant Examiner—William Wicker
Attorney, Agent, or Firm—Jones, Day, Reavis & Pogue

[57] ABSTRACT

This connector assembly comprises a connector body which defines a housing. The housing includes a cavity which is designed to receive a piston, capable of back and forth movement within this cavity. This piston includes a biasing element for urging the piston into the forward direction of the cavity. The piston is engaged with the end of an endoscope tube in the front of this cavity. The piston further includes an orifice which fluidly connects the endoscope tube end to a flexible hose in the back of this piston. The endoscope tube is held in place by jaws which slide back and forth in channels in the front of the connector body, perpendicular to the piston cavity. These jaws also include biasing elements which urge the jaws into mechanical engagement with the rigid tube. Since the jaws in the piston are designed to accommodate a variety of endoscope tube sizes, this connector permits fast, convenient coupling of the flexible hose to the rigid endoscope, minimizing endoscope handling, and thus insuring a greater degree of sterility.

17 Claims, 5 Drawing Sheets

RIGID ENDOSCOPE CONNECTOR

BACKGROUND OF THE INVENTION

This invention relates to a connector for joining a rigid, fluid-carrying tube to a flexible tube. The present invention is particularly useful for the sterilization of endoscopes, which include such a rigid tube, and further include a hollow passage for permitting the fluid flow of a sterilant vapor therethrough.

In order to insure effective sterilant vapor flow through the hollow tube of the endoscope, it has been common in the prior art to attach a flexible hose directly to the endoscope tube. This procedure involves much handling of the endoscope, and thus jeopardizes the overall sterility of the endoscope, particularly upon disengagement.

Many different types of endoscopes are available on the market, with many different sized diameters of endoscope tubes. Also, some of these endoscopes include flanges on the end, having a somewhat smaller diameter than the main endoscope tube diameter, while others do not have these flanges. Thus, it is difficult to attach all of these different diameter endoscope tubes to one common flexible hose.

Further, it is difficult to insure an adequate fluid seal on each of these different diameters using the same flexible hose. An example of such a system employing connectors is shown in copending application, U.S. Ser. No. 851,179, now abandoned, which teaches a sterilization cassette including a plurality of ports for attaching endoscopes thereto.

Consequently, there is a need for a connector which will permit the coupling of all of the many types of endoscopes to one standard flexible hose. Such a connector should permit fast convenient coupling with easy disengagement of the endoscope from the connector, in order to insure the desired level of sterility. Also, this connector must be able to accommodate the many sizes of endoscopes and flanges that are available on the market. This connector must be able to adapt all sizes of endoscopes to one common flexible hose, in such a way as to insure a fluid seal.

SUMMARY OF THE INVENTION

Therefore it is an object of the present invention to provide a connector which permits fast convenient coupling of a rigid endoscope to a flexible hose.

It is another object of the present invention to provide a connector which will accommodate several sizes of endoscopes and flanges to a standard flexible hose.

It is still another object of the present invention to provide a connector which will adapt all sizes of endoscopes to the same hose, and insure a desired fluid seal.

The present invention recites such a connector assembly for removably attaching a rigid tube to a flexible hose. This connector assembly comprises a connector body which defines a housing. The housing includes a cavity which is designed to receive a piston, capable of back and forth movement within this cavity. This piston includes a biasing element for urging the piston into the forward direction of the cavity. The piston is thus urged into mechanical engagement with the end of an endoscope tube in the front of this cavity. The piston further includes a fitting which attaches to a flexible hose in the back of the piston and defines a passage which fluidly connects with the endoscope tube end through an orifice on the front face of the piston.

The endoscope tube is held in place by jaws which slide back and forth in channels in the front of the connector body, perpendicular to the piston cavity. These jaws also include biasing elements which urge the jaws into mechanical engagement with the rigid tube. Since the jaws and the piston are designed to accommodate a variety of endoscope tube sizes, this connector permits fast, convenient coupling of the flexible hose to a rigid endoscope, minimizing endoscope handling, and thus insuring a greater degree of sterility. The present connector also permits several sizes of endoscopes to be so connected, whether or not these include flanges. The present connector can adapt all sizes of endoscopes to the same hose and insure the proper fluid seal.

Additional objects, advantages and novel features of the inventions will be set forth in part in the description which follows, and in part will become apparent to those skilled in the art upon examination of the following or maybe learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and form a part of the specification, illustrate several preferred embodiments of the present invention and, together with the description, serve to explain the principles of the invention. In the drawings.

DETAILED DESCRIPTION OF THE PREFERRED EMBODIMENTS

Figure 1:
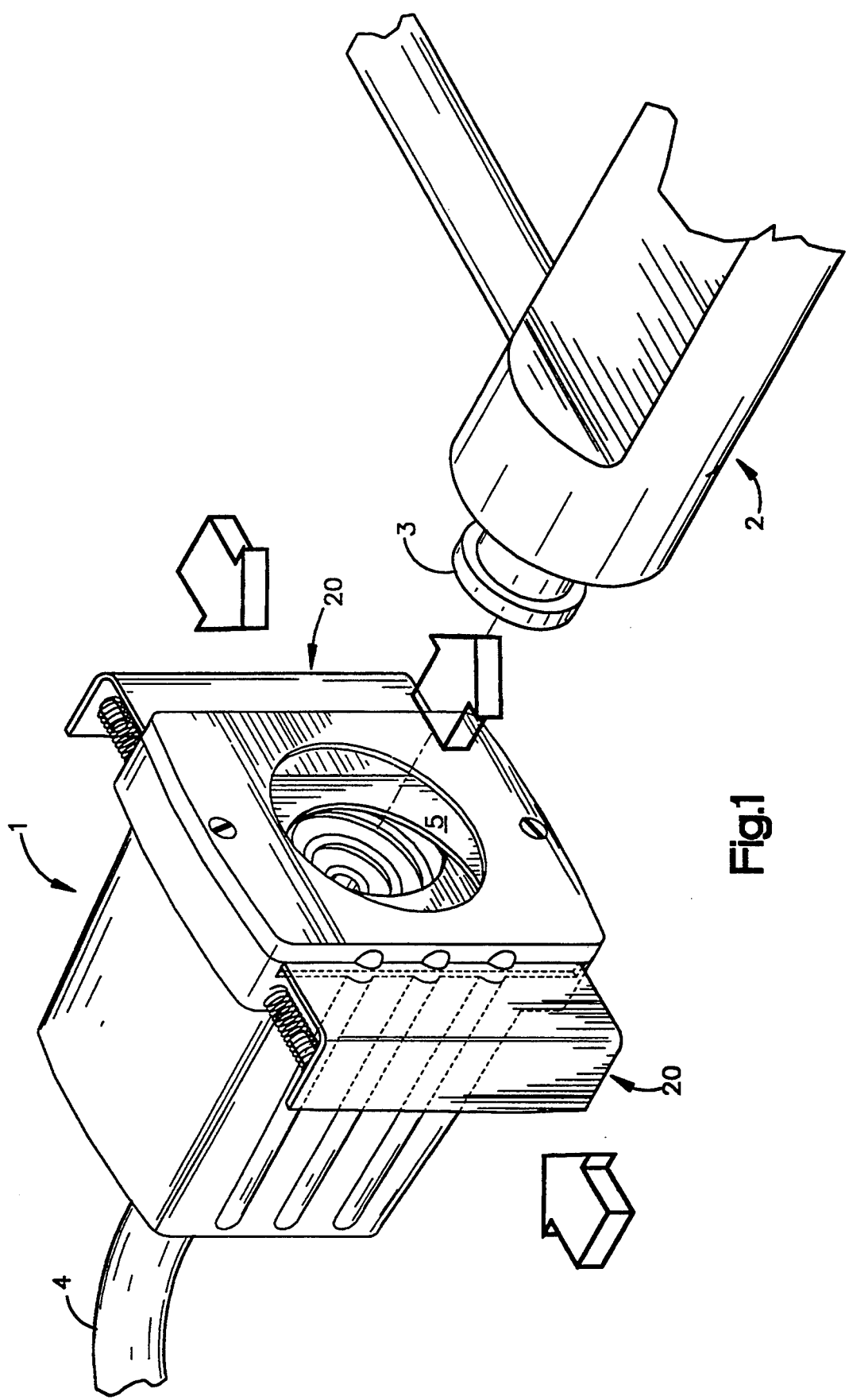
FIG. 1 is a perspective drawing showing a first preferred embodiment of the present invention.

Reference will now be made in detail to the present preferred embodiment of the invention, an example of which is illustrated in the accompanying drawings. FIG. 1 shows a first preferred embodiment of the present invention, wherein rigid endoscope connector 1 is poised to receive the end of endoscope 2. The connector 1 is joined with a flexible hose 4, which is in turn connected to a source of sterilant vapor. The endoscope 2 includes a flange 3 with a diameter somewhat narrower than the endoscope tube itself. The connector 1 includes an aperture 5 which is configured to admit the flange end of the rigid endoscope 2. The endoscope 2 is admitted into the connector 1 by applying force to the two jaws 20 on the exterior of the connector 1. This applied force opens up a gap between the two jaws which permits entry of the flange end into the connector 1.

Figure 2:
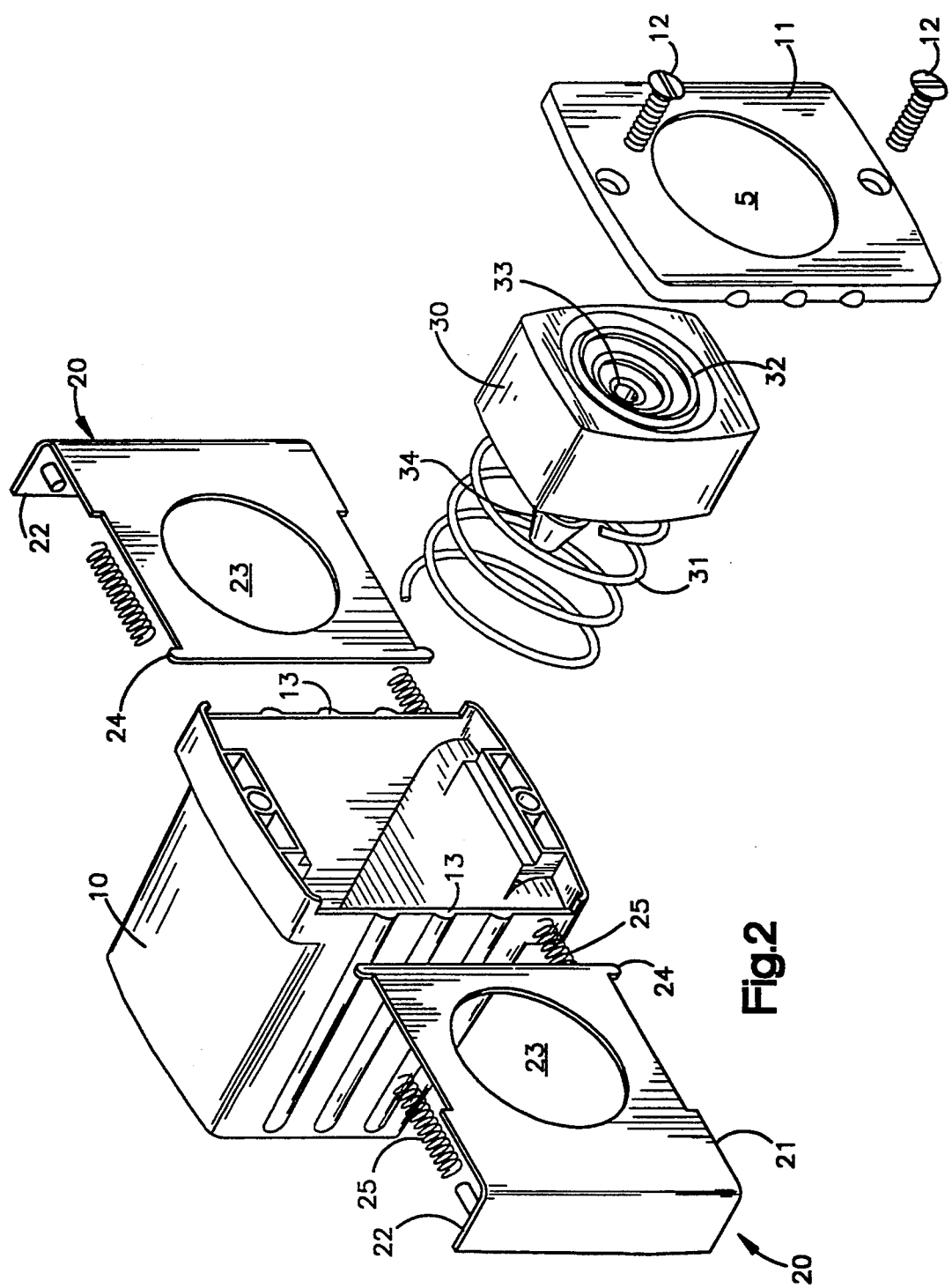
FIG. 2 shows an exploded view of the first preferred embodiment of the present invention.

Turning now to FIG. 2 we see the components of the first preferred embodiment of the present invention. This first preferred embodiment of the present rigid endoscope connector 1 includes a connector body 10. The moving parts are encased within this connector body 10 whose function it is to contain and provide mounting and guiding surfaces for all the moving parts. The connector body 10 is hollow, and defines a housing including a central longitudinal hollow cavity. Inside this cavity there is fitted a piston 30. This piston 30 is urged away from the interior back wall of the connector body 10 by a piston spring 31. The piston spring 31 may be a coil spring. At the rear end of this piston 30, there is a hose fitting 34 which is tapered so as to attach with the flexible hose 4 with an interference fit.

The front of the piston 30 includes a concave piston face 32 which is designed to receive a variety of diameters of rigid endoscope tubes 2 so as to provide fluid connection therewith. This surface is concave to provide better alignment and linear contact between the endoscope tube 2 and the piston 30. At the center of this concave piston face 32 there is an orifice 33 which runs the length of the piston and connects with the hose fitting 34, defining a hollow fluid conducting channel.

Attached to the connector body 10 is a cover plate 11, which includes the aperture 5, and is held in place with screws 12. This cover plate 11 retains the piston 30 in the connector body 11, against the force of the piston spring 31. The flange 3 of rigid endoscope tube 2 is inserted through the aperture 5 of this cover plate 11, to be received in fluid connection with the concave piston face 32.

The rigid endoscope tube 2 is retained in fluid connection with the piston 30 by means of jaws 20 which retain the rigid endoscope 2. Each of these jaws 20 include a jaw plate 21 which is integrally conjoined at a perpendicular angle to a capture plate 22. Each jaw plate 21 is designed to slide back and forth along channels 13 which have been defined in the front of the connector body 10. Each jaw plate 21 includes an aperture 23 which is sized to receive many sizes of rigid endoscope tubes 2. The jaw 20 is biased in an outward direction from the connector body 10 by means of jaw springs 25, which apply on outward force to each capture plate 22. The jaws are retained inside the connector body 11 by means of stops, shown as projections 24. The jaw springs 25 urge the respective jaw plates 21 in transverse opposite directions, each away from their respective sides of the connector body 10.

The connector 1 is designed to be put on the endoscope 2 in the following manner: The jaws 20 are squeezed between the thumb and forefinger of an operator until the apertures 23 in the jaws 20 are concentrically aligned with each other and the piston 30. The end of the endoscope 2 is inserted into these open apertures 23, and is pushed against the concave piston face 32. The abutment of the endoscope 2 against the piston 30 depresses the piston spring 31 until the flange 3 of the endoscope 2 is on the interior of the jaws 20. The jaws 20 are then released and closed around the telescope.

The concave piston face 32 maintains contact with the end of the endoscope 2 due to the force exerted by the piston spring 31. For an unflanged endoscope 2, the depth of insertion into the body must be sufficient for the connector 1 to be securely retained on the endoscope. When the rigid endoscope tube 2 is inserted through the apertures 23 of the jaws, the outward biasing force of the springs causes the interior edges along each aperture 23 to grip the rigid tube 2. This gripping force is sufficient to insure a fluid connection between the flange end 3 of rigid endoscope tube 2 and the concave piston face 32. The rigid endoscope tube 2 may then be disengaged from the connector 1 by applying force to the jaws 20, thus releasing the tube 2 from engagement with the piston 30.

Figure 3:
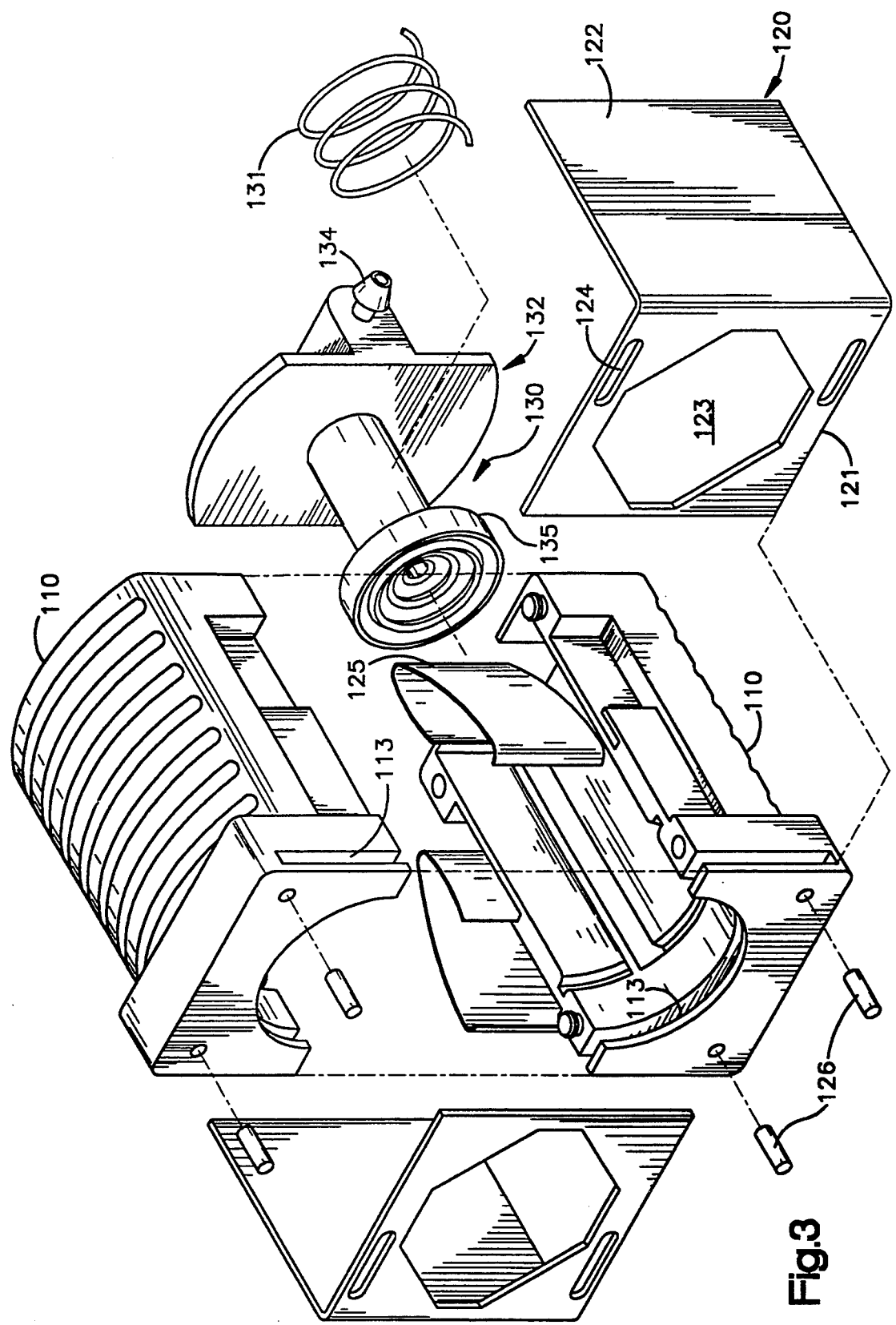
FIG. 3 shows an exploded drawing of the second preferred embodiment of the present invention.

A second preferred embodiment of the present invention is shown in FIG. 3, which operates according to a concept similar to that of first preferred embodiment. The connector body is in the form of two half-body sections 110 which are each identical. When assembled, the half-body sections 10 retain a piston 130 which includes a back plate 132 that remains outside of the assembled connector body, but has a piston flange 135 which extends into the cavity defined by these assembled half-body sections 110. The piston flange 135 is urged toward the front of the piston cavity by means of an open-end coil spring 131, inserted between the piston flange 135 and the back wall of the assembled half-body sections 110. The back plate 132 also includes a hose fitting 134 which may be set at a perpendicular angle to the motion of piston 130.

Each half body section 110 includes connector body channels 113 which are dimensioned to receive jaws 120. Each of these jaws 120 are in sliding engagement with each other along the interior of these connector body channels 113. Each jaw 120 includes a jaw plate 121 with an integral perpendicular capture plate 122 and an aperture 123, all with a similar function to that of the previous embodiment. In an alternative embodiment, the aperture 123 may be generally diamond-shaped.

Each jaw 120 is retained in the connector body channels 113 by a cooperating arrangement of jaw channels 124, which are described along the face of the jaw plate 121, in cooperation with retaining pins 126, which are fixedly inserted into each half body section 110. These retaining pins 126 limit the outward travel of the jaws 120 within the motion permitted by jaw channels 124. As in the previous embodiment, the capture plate 122 is urged away from the connector body by means of a spring, in this alternative embodiment, leaf spring 125. The connector half-body sections 110 may be fixed together using an arrangement of knobs and holes to produce respective interference fits.

Figure 4:
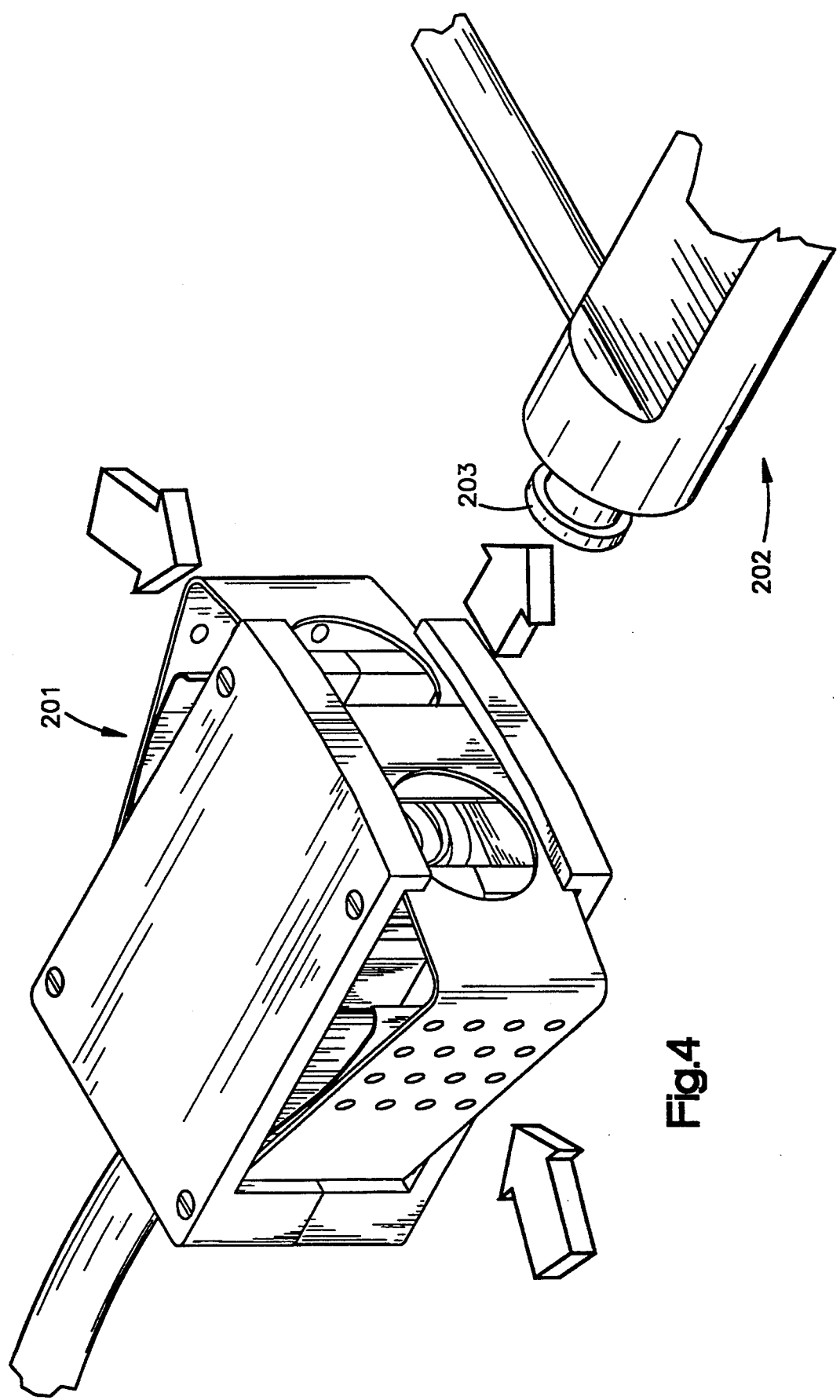
FIG. 4 shows a perspective view of the third preferred embodiment, representing an alternative concept of the present invention.
Figure 5:
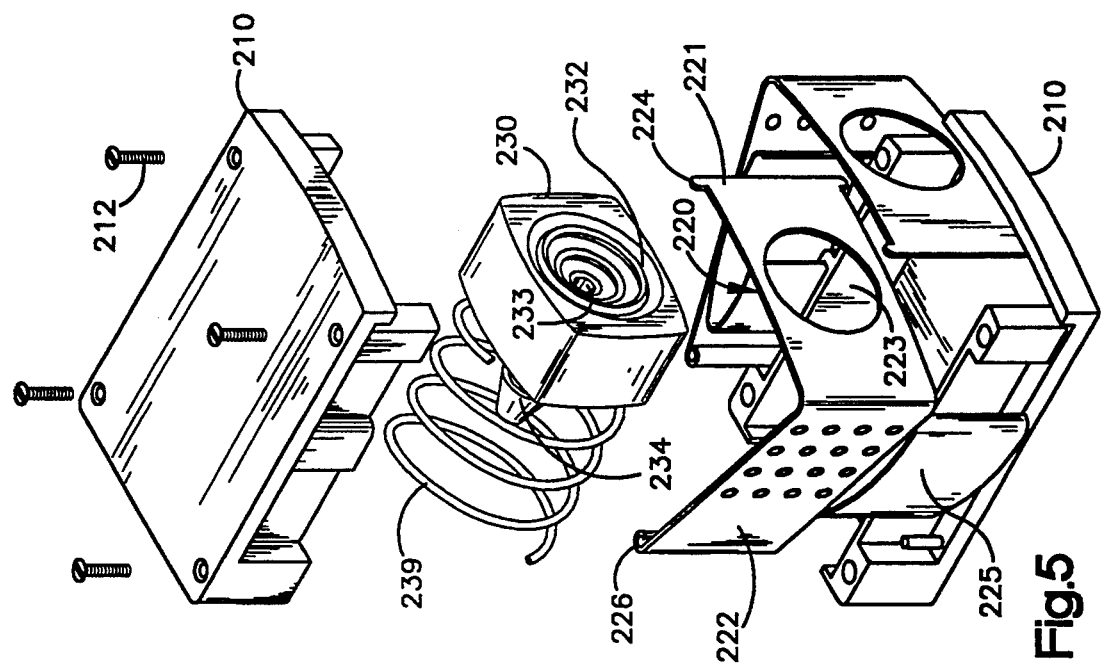
FIG. 5 shows an exploded view of the third preferred embodiment of the present invention.

An alternative concept of the present invention is shown in the third preferred embodiment of the rigid endoscope connector 201, seen in FIG. 4, with particular reference to the exploded view of FIG. 5. This embodiment includes a piston arrangement identical to that shown in the first preferred embodiment, including concave piston face 232, hose fitting 234, and orifice 233, with the entire piston 230 being urged away from the interior back wall of the connector body 210 by way of a piston spring 231. In this third preferred embodiment of the present invention, the jaws 220 are permitted to pivot.

As seen in FIG. 5, the connector body includes identical half-body sections 210 which are fixed together with screws 212. Each half body section includes a plurality of elongated projections 213 which extend from each half-body section 110 in such a way that opposing elongated projections 213 on each half-body section 110 are collinear when these sections are assembled. Each jaw 220 includes a jaw plate 221, capture plate 222, and apertures 223. The capture plate 222 is urged away from the connector body by leaf spring 225, and its outward motion is limited by a stop, shown as projections 224.

In the alternative concept shown in this embodiment, each jaw 220 is permitted to pivot along an integral hinge 226 which cooperates with the respective elongated projections 213 extending from half-body section 210. This pivoting insures an optimal and uniform transmission of force from the leaf spring 225 to the jaw members 220.

Figure 6:
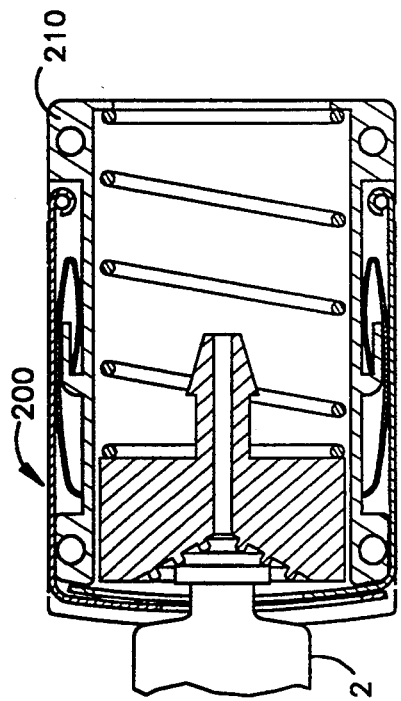
FIG. 6 shows a sectional view of the third embodiment of the present invention, illustrating the engagement of the endoscope.
Figure 7:
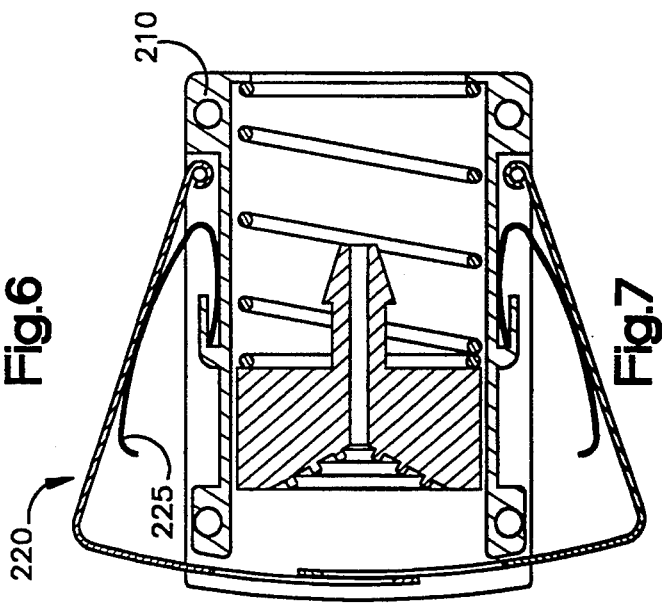
FIG. 7 shows a sectional view of the present of the third preferred embodiment of the present invention when the endoscope is not engaged.

FIG. 6 shows a sectional view of the connector 201 of the third embodiment when it is disengaged from the flange end 3 of the rigid endoscope tube 2. In this figure we see the jaws 220 urged away from the connector body sections 210 by the leaf spring 225. The action of this leaf spring upon the jaws of this embodiment causes the jaw plates 221 to describe arcs as they pivot back and forth along the front surface of the connector 201, as limited by the hinge 226. As an inwardly directed force must be applied to each jaw 220 in order to admit the rigid endoscope tube 2 into the connector body 210, this opposing force permits significant securement of the endoscope tube 2, as is shown in FIG. 7.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention and various embodiments and with various modifications as are suited to the particular use contemplated. It is intended that the scope of the invention be defined by the claims appended hereto.

What is claimed is:

1. A connector assembly for removably attaching a rigid tube to a flexible hose, the connector assembly comprising:
    a connector body which defines a housing, including a cavity which extends along a longitudinal axis and channels perpendicular to the longitudinal axis of said cavity;
    a piston configured to reside within the connector body cavity and dimensioned to permit reciprocating motion along the longitudinal axis of the cavity, and including first biasing means for urging said piston toward a side of said cavity proximate said channels to engage said rigid tube; said piston is attached to said flexible hose and includes an orifice to permit fluid connection with said flexible hose; and
    first and second jaw plates, movably retained within said channels so as to permit reciprocating movement therealong, each jaw plate including an aperture with an interior side, further including second biasing means for urging the jaw plates into opposing directions, so as to bias the interior sides into mechanical engagement with said rigid tube.

2. The connector assembly of claim 1 wherein said jaw plates include stops to limit the direction of travel in response to the force of the second biasing means.

3. The connector assembly of claim 1 wherein the connector body is of unitary construction and includes a plate that is secured to the connector body to retain the piston and jaw means within the housing.

4. The connector assembly of claim 1 wherein the connector body is of two-piece construction with the respective pieces secured to retain the piston and jaw means within the housing.

5. The connector assembly of claim 1 wherein the piston includes a hose fitting which is tapered to permit an interference fit with said flexible hose.

6. The connector assembly of claim 1 wherein the piston includes a concave region with annular descending ridges described therein.

7. The connector assembly of claim 6 wherein the concave region is formed on the piston body.

8. The connector assembly of claim 6 wherein the concave region is formed on a flange which extends from the piston body.

9. The connector assembly of claim 1 wherein said jaw means includes capture plates, formed integrally with and perpendicular to each of said jaw plates, and said second biasing means comprising jaw springs for applying force to each respective capture plate in order to urge each jaw plate in an opposing direction to the other.

10. The connector assembly of claim 9 wherein said jaw springs are coil springs.

11. The connector assembly of claim 9 wherein said jaw springs are leaf springs.

12. The connector assembly of claim 9 wherein said jaw springs urge said capture plates away from said connector body so as to displace the apertures, whereby the jaw springs must be stressed to permit the admission of the rigid tube, whereby the spring force is sufficient to retain said rigid tube between the jaw apertures.

13. The connector assembly of claim 12 wherein each said capture plate includes a hinge piece which cooperates with elongated projections extending from the connector body to permit a pivoting motion of the jaw plates.

14. The connector assembly of claim 12 wherein said jaw apertures are circular.

15. The connector assembly of claim 12 wherein said jaw apertures are generally diamond-shaped.

16. The connector assembly of claim 15 wherein said stops comprise projections, coplanar with the jaw plate, and perpendicular to the biasing direction.

17. The connector assembly of claim 15 wherein said stops comprise jaw channels in each jaw plate, parallel to the biasing direction, which cooperate with respective pins that are fixedly mounted on the front surface of the connector body.

* * * * *